(12) United States Patent
Kuan et al.

(10) Patent No.: US 9,063,128 B2
(45) Date of Patent: *Jun. 23, 2015

(54) THREE DIMENSIONAL LIGNOCELLULOSIC DETECTION DEVICE

(71) Applicant: National Tsing Hua University, Hsinchu (TW)

(72) Inventors: Chen-Meng Kuan, Hsinchu (TW); Robert S. Langer, Hsinchu (TW); Chao-Min Cheng, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 47 days.

This patent is subject to a terminal disclaimer.

(21) Appl. No.: 13/945,237

(22) Filed: Jul. 18, 2013

(65) Prior Publication Data

US 2014/0377787 A1    Dec. 25, 2014

(30) Foreign Application Priority Data

Jun. 25, 2013    (TW) .............................. 102122514 A

(51) Int. Cl.
*G01N 33/52* (2006.01)
*C12Q 1/54* (2006.01)

(52) U.S. Cl.
CPC ...... *G01N 33/52* (2013.01); *C12Q 1/54* (2013.01); *G01N 33/528* (2013.01)

(58) Field of Classification Search
CPC ........ C12Q 1/6816; C12Q 1/25; G01N 33/48; G01N 33/50; G01N 33/52; G01N 33/525; G01N 21/00; G01N 21/75; G01N 21/77; G01N 21/78
See application file for complete search history.

(56) References Cited

U.S. PATENT DOCUMENTS

| 3,552,928 A | 1/1971 | Fetter |
| 2010/0159599 A1* | 6/2010 | Song et al. ...................... 436/39 |
| 2013/0034869 A1* | 2/2013 | Whitesides et al. ......... 435/7.92 |

FOREIGN PATENT DOCUMENTS

| TW | 201017165 A | 5/2010 |
| TW | 201226904 A | 7/2012 |

OTHER PUBLICATIONS

Sun, Y. et al. 2002. Hydrolysis of lignocellulosic materials for ethanol production: a review. Biosource Technology 83: 1-11. specif. p. 2.*

* cited by examiner

*Primary Examiner* — John S Brusca
*Assistant Examiner* — Sharon M Papciak
(74) *Attorney, Agent, or Firm* — Muncy, Geissler, Olds & Lowe, P.C.

(57) ABSTRACT

A three dimensional lignocellulosic detection device includes a first lignocellulosic substrate and a second lignocellulosic substrate. When the first lignocellulosic substrate is in contact with a liquid specimen through capillary effect, the sample is absorbed into the second lignocellulosic substrate through the first lignocellulosic substrate, reacts with the detecting reagent on the second lignocellulosic substrate and makes a detection test. The three dimensional lignocellulosic detection device of the present invention has the inherent advantages of a lignocellulosic material such as natural material, low cost, easy manipulation and capillary effect and results in a good preventive diagnostic platform. Also, users may achieve preventive disease diagnostic without spending additional time and/or money.

9 Claims, 4 Drawing Sheets

Glucose concentration  0mM   2.5mM   10mM   50 mM

Average intensity  154    169    207    210

THREE DIMENSIONAL LIGNOCELLULOSIC DETECTION DEVICE

BACKGROUND OF THE INVENTION

1. Field of the Invention

The present invention relates to a detection device, and particularly relates to a three dimensional lignocellulosic detection device achieved by capillary action.

2. Description of the Prior Art

With the increasing trend in people's health awareness, the concept of self-testing at home has gradually prevailed. Self-test kits provide tests that people may perform tests at home at any time and may be achieved by observing the color change of the detection reagent. Therefore, disease signs may be immediately observed with simple instruments or unaided eyes instead of complex instruments. In addition, when the color changes grow larger, users may go to the hospital for further detailed examination. Therefore, self-test kits have advantages in immediate facilitation and saving money.

Regarding self-test kits used at home, test strips have been frequently used. Test strips have advantages such as simple operation, easy to interpret and easy to carry. The principle of test strip detection is achieved by biochemical reactions catalyzed by the enzyme and specific substances so as to produce changes in color or other properties, and a qualitative reaction for detection the presence of a substance or a semi-quantitative reaction for determining the concentration of the substance may thus be achieved.

For example, a glucose oxidase method applied in home-use blood sugar or urine glucose test strips refers to the color changes in test strip achieved by the specificity of the catalytic reaction between glucose oxidase and glucose while other reducing substances does not work. A test strip coated with a glucose oxidase using enzyme technology would result in color changes after the reaction of glucose oxidase and glucose in the blood, so that the user may interpret glucose concentration level based on comparison result of the color of the test strip with the color chart.

This simple blood glucose measurement method has been found beneficial to many patients with diabetes, such as monitoring disease at any time in terms of improving quality of life as well as expanding scope of medical care. However, the convenience of the test strip is still room for improvement since the test strip is still in need of special carry. Therefore, the development of a testing platform, which has the advantages of the test paper and has the convenience of matching with the daily necessities, is a current goal.

SUMMARY OF THE INVENTION

It is therefore an objective of the present invention to provide a detection platform having the advantage of the test strip and the convenience of matching articles for daily use.

According to one embodiment of the present invention, a three dimensional lignocellulosic detection device comprises a first lignocellulosic substrate and a second lignocellulosic substrate. The first lignocellulosic substrate has a contact area and at least a groove. The second lignocellulosic substrate is arranged in the groove of the first lignocellulosic substrate, wherein materials of the first lignocellulosic substrate and the second lignocellulosic substrate are different. The second lignocellulosic substrate comprises at least a detection reagent. When a liquid specimen contacts the contact area of the first lignocellulosic substrate, the liquid specimen is absorbed into the first lignocellulosic substrate and flows to the second lignocellulosic substrate relying on capillarity, and the liquid specimen reacts with the detection reagent of the second lignocellulosic substrate to achieve the detection of the liquid specimen.

The objective, technologies, features and advantages of the present invention will become apparent from the following description in conjunction with the accompanying drawings wherein certain embodiments of the present invention are set forth by way of illustration and example.

DESCRIPTION OF THE PREFERRED EMBODIMENT

The present invention relates to a lignocellulosic detection device with the main elements, lignocellulosic substrate and detection reagent.

The lignocellulose, or called lignified tissue, is generally known as the plant tissue inwardly formed by the vascular cambium. Besides, the lignocellulose is generally obtained from the lignified tissue formed by arbor and bush. Comparing to the filter paper detection devices, the lignocellulose is resistant to strong-acid and/or organic solvents. The lignocellulose also has a tenacious mechanical structure that may keep complete structure and mechanical strength after being dipped into the liquid. Hence, the lignocellulose has advantages in structural strength than the filter paper.

Furthermore, comparing to the filter paper of the two dimensional detection device, the lignocellulosic detection device in the present invention is a three dimensional structure that has an additional flexibility of detection.

Figure 1:
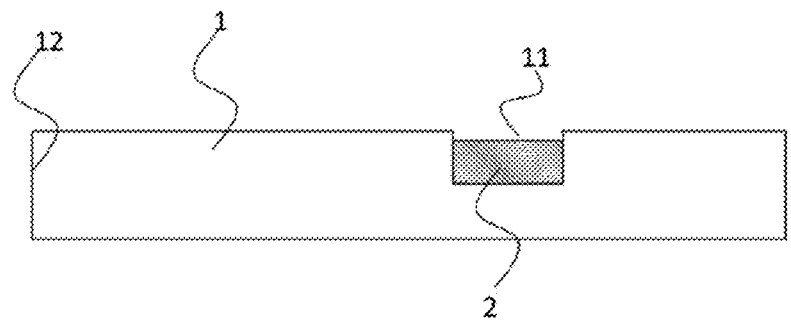
FIG. 1 is a schematic diagram of the lignocellulosic detection device of the present invention.

Please refer to FIG. 1 which is a schematic diagram of the three dimensional lignocellulosic detection device of the present invention. The first lignocellulosic substrate 1 has a contact area 12 and a groove 11. Generally speaking, shape or size of the groove 11 is not specifically limited and may be designed according to actual requirements. It's noted that the shape of the groove 11 in FIG. 1 is only used for illustration without any limitation to the present invention. Generally speaking, the shape of the groove 11 comprises cuboid, cube, cylinder, hemisphere, V-shaped or the combination of other shapes. The position of the groove 11 may be also flexibly designed according to actual detection requirements.

The shape or size of the first lignocellulosic substrate 1 is not specifically limited and may be designed according to actual detected target. The shape of the general lignocellulosic substrate includes, but not limited to, cylinder, cuboid, plank and so on.

The second lignocellulosic substrate 2 may be arranged in the groove 11 as a detection area, so that the detection reagent may be arranged in the second lignocellulosic substrate 2 to process the detection. The second lignocellulosic substrate 2 may be higher, equal to or lower than the groove 11.

The method of arranging the second lignocellulosic substrate 2 in the groove 11 is not specifically limited, and the purpose is to make the first lignocellulosic substrate 1 and the second lignocellulosic substrate 2 in contact with each other. The method comprises, but not be limited to, inlaying the second lignocellulosic substrate 2 into the groove 11, gluing the second lignocellulosic substrate 2 into the groove 11, or simply placing the second lignocellulosic substrate 2 into the groove 11.

The materials of the first lignocellulosic substrate 1 and the second lignocellulosic substrate 2 are different, and furthermore, the material of the second lignocellulosic substrate 2 is denser than the material of the first lignocellulosic substrate 1. Besides, the flowing rate of the liquid specimen in the first lignocellulosic substrate 1 is faster than the flowing rate of the liquid specimen in the second lignocellulosic substrate 2.

The present invention may utilize the capillarity provided by the internal water pipes (not shown in figures) of the first lignocellulosic substrate 1 to transfer the detected target to the detection area, the groove 11. It may prevent the surface water pipes of the first lignocellulosic substrate 1 being physically damaged in the manufacturing process and causing the measurement error, and furthermore, control the flowing rate of the liquid specimen. The position of the contact area 12 of the first lignocellulosic substrate 1 is preferably arranged at both ends of the first lignocellulosic substrate 1.

It's understood that the detected target may be transferred to the detection area, the groove 11, by utilizing the capillarity provided by the internal water pipes (not shown in figures) of the first lignocellulosic substrate 1. Using the internal water pipes of the first lignocellulosic substrate 1 may prevent the surface of the first lignocellulosic substrate 1 being physically damaged in the manufacturing process and causing the measurement error, and furthermore, control the flowing rate of the liquid specimen. The contacting position of the specimen and the first lignocellulosic substrate 1 is preferably arranged at both ends of the first lignocellulosic substrate 1.

The surface of the first lignocellulosic substrate 1 may be further processed to enhance the stability of the lignocelluloses. The surface process is like, but not limited to, waterproof process. The waterproof reagent comprises, but not limited to, Polydimethylsiloxane (PDMS).

In one embodiment, the first lignocellulosic substrate 1 may be articles for daily use, which comprises, but not limited to, the stirrer, the toothpick or the wooden chopstick.

In one embodiment of the present invention, the material of the first lignocellulosic substrate 1 is bamboo composed of lignocelluloses, and the bamboo material is very popular in Asia. The trunk of bamboo plant is ligneous, like bush or arbor, and this material has the advantage in price since the bamboo's fast growth.

The advantages of using the toothpick are natural, cheap and convenient to manufacture. The toothpick is generally used after having a meal to keep the mouth clean. One purpose of the present invention is to make the users completing the detection while they are using the toothpick to clean their mouths.

As described above, the material of the second lignocellulosic substrate 2 is denser than the material of the first lignocellulosic substrate 1. The material of the second lignocellulosic substrate 2 comprises, but not limited to, birch, poplar or pine.

The method of arranging the detection reagent in the second lignocellulosic substrate 2 is not specifically limited, and the preferred one is evenly absorbed or spread into the second lignocellulosic substrate 2. It's understood that the detection reagent may be also arranged on single side, bottom side, double sides or other combination of the second lignocellulosic substrate 2.

The method of absorbing the detection reagent in the second lignocellulosic substrate 2 includes, but not limited to, immobilizing the detection reagent solution into the second lignocellulosic substrate 2. Relying on the capillarity of the second lignocellulosic substrate 2 and the bundle tissue of the plant fiber, the detection reagent may be absorbed in the second lignocellulosic substrate 2. After immobilizing the detection reagent solution into the second lignocellulosic substrate 2, a drying step may be further performed to complete the lignocellulosic substrate for detection.

The lignocellulosic substrate of the present invention may utilize the colorimetric reaction or the fluorescence to detect, wherein the detection reagent comprises a coloring agent or a fluorescent reagent. The coloring agent or the fluorescent reagent of the detection reagent may be adaptively changed according to the detected target.

In one embodiment of the present invention, the detection reagent comprises an enzyme. As described above, the enzyme may react with specific material in the solution to result the change of color or other characteristics and detect the qualitative reaction of specific material and the quantitative reaction of material concentration. For example, the detection principle of the "glucose oxidase method" is utilizing the specificity catalytic reaction between the glucose oxidase and the glucose to evaluate the concentration of glucose via the color change.

The liquid specimen includes, but not limited to, saliva, blood, urine or other body fluid of a user. As described above, the liquid specimen is absorbed into the fiber tissue of the first lignocellulosic substrate 1 relying on the capillarity, and the liquid specimen reacts with the detection reagent to complete the detection. Besides, the solid detected target may be suspended in the liquid solution, and the above detection method relying on the capillarity may be performed after the detected target is dissolved into the solution.

It's noted that the multiple detection may be multiple qualitative or quantitative, which means the multiple detection may includes the detection of multiple detected target or multiple concentration of one detected target.

The principle of the present invention is utilizing the capillarity of the lignocelluloses to make the lignocellulosic substrate being a detection platform of disease prophylaxis. The detection reagent absorbed in the fiber tissue of the second lignocellulosic substrate 2 is utilized in the present invention. When the first lignocellulosic substrate 1 contacts a liquid specimen or a specimen having liquid, the target specimen is absorbed into the fiber tissue of the lignocellulosic substrate relying on capillarity and reacted with the detection reagent to complete the detection.

It's noted that the first lignocellulosic substrate in the present invention is generally used in taking food or drink, such as cleaning the mouth after the meal, and so that a preferred embodiment is using a user's saliva to detect. The advantage of using the saliva is that the saliva detection is non-invasive and easy to collect, the cost is low, the risk of infection is low, and the patients may collect and detect by themselves without assistance from medical personnel.

As described above, the lignocellulosic substrate of the present invention may be used for detecting biochemical characters of user's saliva, blood, urine or other body fluid, such as, but not limited to, detecting glucose, nitrite or pH value. The embodiment below is used to explain the detection principle and application.

1. Nitrite Detection

The nitrite in food will be changed into nitrite amine after reacting with the digestive enzyme in saliva, and the nitrite amine is approved as a carcinogen. Besides, the drinking water, vegetable, food, fish, meat product or pickled vegetables with great quantity of nitrite may directly intoxicate people. The conventional nitrite test strip utilizes the chemical coloring reaction to detect, so that the nitrite detection of food is also a suitable application of the present invention.

2. Glucose Detection

The principle of detecting blood sugar or urine sugar is described above that may help the patients to monitor their situation by themselves at any time.

3. pH Value Detection

When detecting the pH value, the litmus paper is the most popular tool to measure the pH value of a solution. The manufacture process of the litmus paper is dipping papers into solution having the litmus reagent. The litmus paper shows red in acid liquid and blue in alkaline liquid, so that may apply to the lignocellulosic substrate of the present invention to detect the pH value.

In order to make the objectives, technical solutions and advantages of the embodiments of the present invention clearer, the embodiments of the present invention are further described in detail below with reference to the embodiments and accompanying drawings. Here, the exemplary embodiments and the illustrations of the present invention are only intended to explain the present invention, rather than limit the present invention.

Figure 2:
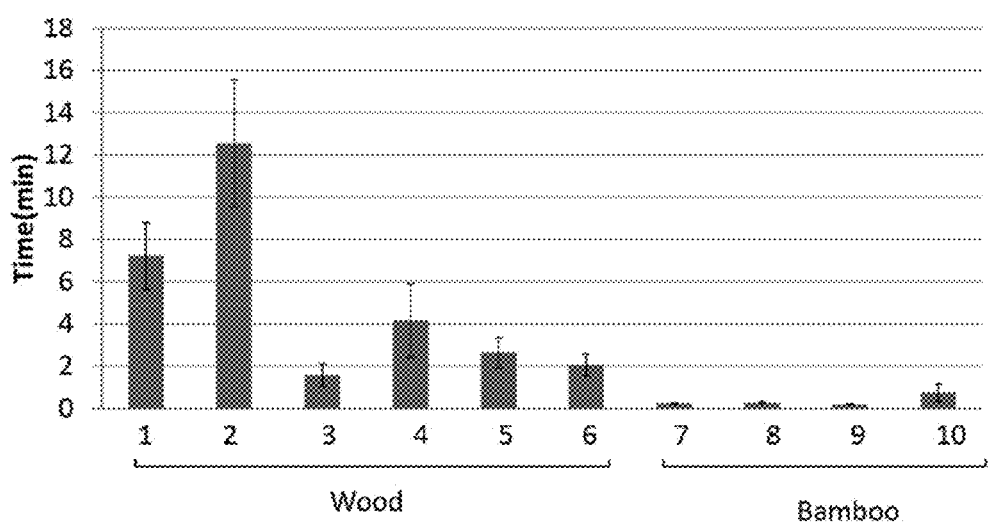
FIG. 2 is a histogram showing the flowing rate of liquid in the lignocellulosic substrate.

The Comparison of the First Lignocellulosic Substrate and the Second Lignocellulosic Substrate:

Please refer to FIG. 2 which is a histogram showing the flowing rate (n=8) of liquid in the lignocellulosic substrate. The lignocellulosic substrate is the coffee stirrer or bamboo stick in the market. The flowing time of liquid in the bamboo lignocellulosic substrate is shorter than that in the wood lignocellulosic substrate, so that the flowing rate of liquid in the bamboo lignocellulosic substrate is faster than that in the wood lignocellulosic substrate.

Figure 3:
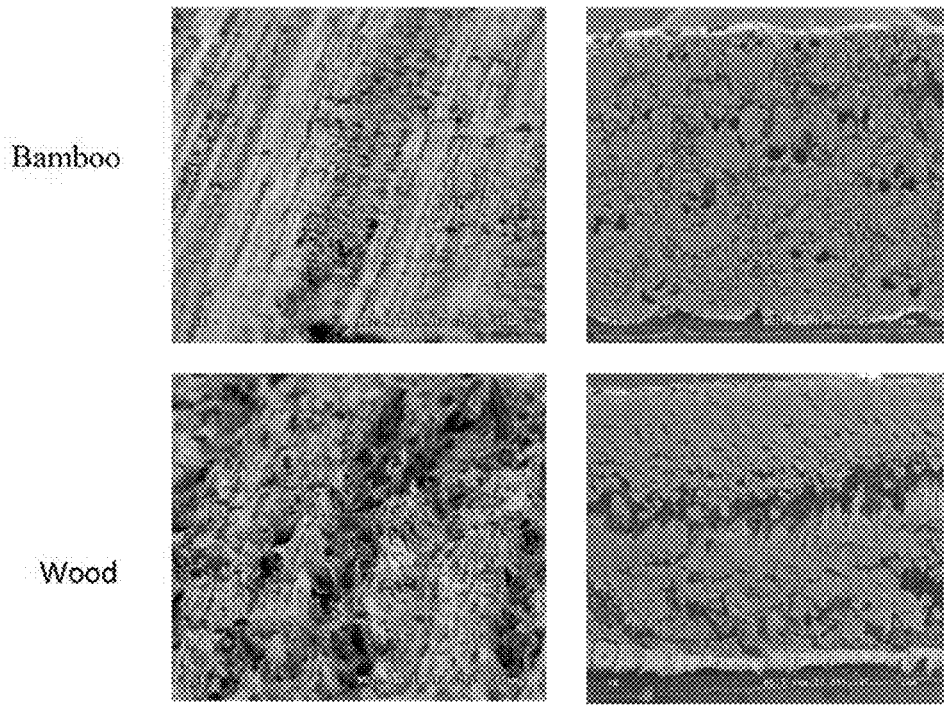
FIG. 3 illustrates microscopic pictures of the lignocellulosic substrate.
Figure 4:
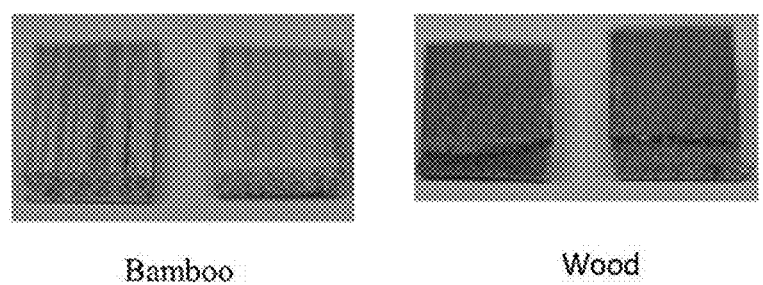
FIG. 4 illustrates pictures showing the dye absorption of the lignocellulosic substrate.

Please further refer to FIG. 3 which illustrates microscopic pictures of the lignocellulosic substrate, and FIG. 4 which illustrates pictures showing the dye absorption of the lignocellulosic substrate. The wood lignocellulosic substrate is denser than the bamboo lignocellulosic substrate and the coloring result is more even, so that the dye absorption of the wood lignocellulosic substrate is more even than that of the bamboo lignocellulosic substrate.

Experiment of Detection Reagent Absorption of the Lignocellulosic Substrate:

Experiment steps: using the pipetman to drip 2 μL nitrite detection reagent on the wood stirrer, wherein the nitrite detection reagent comprises 50 mmol/L sulfanilamide, 330 mmol/L citric acid and 10 mmol/L N-(1-naphthyl)ethylenediamine. After drying the stirrer, the lignocellulosic substrate having nitrite detection reagent may be used for contacting the nitrite solution to detect the nitrite.

Figure 5:
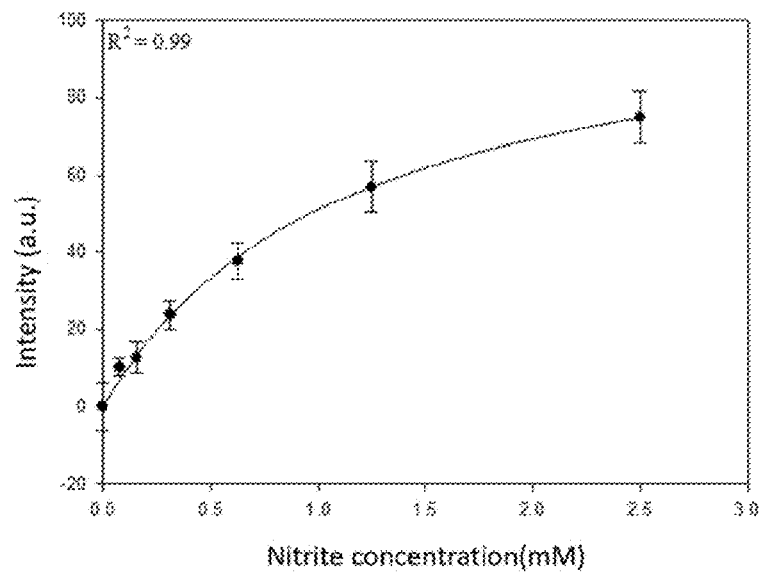
FIG. 5 is a schematic diagram showing the nitrite absorption of the lignocellulosic substrate.

FIG. 5 is a schematic diagram showing the nitrite absorption of the lignocellulosic substrate. It shows the positive dependence ($R^2$=0.99) when the concentration is below 2.5 mM. It's noted that the data in this embodiment is not performed by the three dimensional detection, and it merely uses the groove on the stirrer to detect the nitrite.

Manufacturing of the Three Dimensional Lignocellulosic Substrate

Obliquely cut an opening on the bamboo stirrer and inlay the wood stirrer into the obliquely cut groove of the bamboo stirrer to obtain the three dimensional lignocellulosic substrate of the present invention.

Detecting the Nitrite with the Three Dimensional Lignocellulosic Substrate

Figure 6:
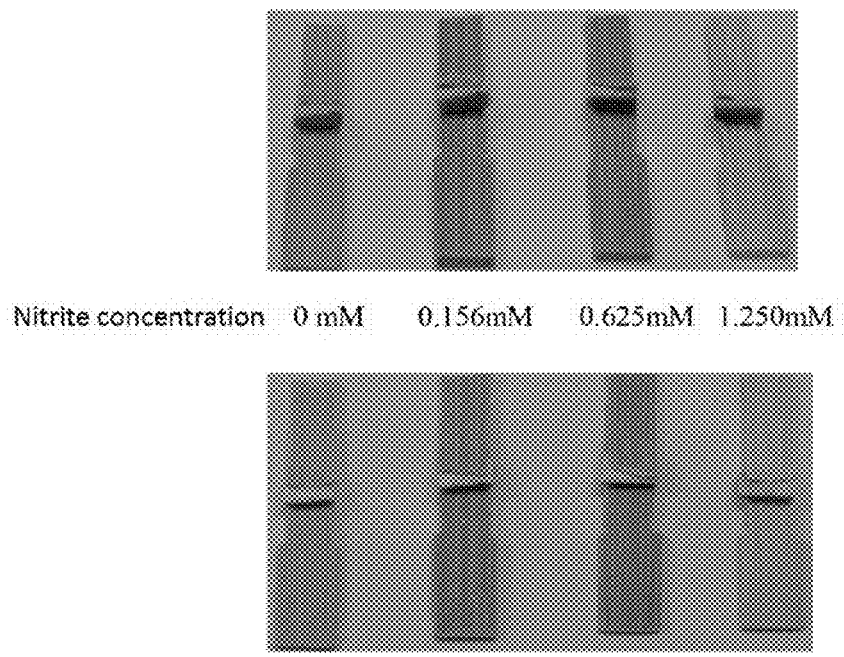
FIG. 6 illustrates pictures showing the detection result of the three dimensional lignocellulosic detection device used for detecting nitrite.

Let the three dimensional lignocellulosic substrate spread the nitrite detection reagent contacts the nitrite solution to detect the nitrite. Please refer to FIG. 6 which illustrates pictures showing the detection result of the three dimensional lignocellulosic detection device used for detecting nitrite. The qualitative result shows that the red coloring result on the detection area of the wood stirrer becomes darker and even with the increasing of nitrite concentration. The color difference with the control group may be observed by naked eye on the concentration 0.156 mM.

Detecting the Glucose with the Three Dimensional Lignocellulosic Substrate

Let the three dimensional lignocellulosic substrate spread the glucose detection reagent contacts the glucose solution to detect the glucose, wherein the glucose detection reagent (2 μL) comprises Glucose oxidase 75 units/mL, HRP 15 units/mL, 10 mM dimethylaminobenzoic acid, 2 mM 4-aminoantipyrine, 10% (w/v) PEG (MW=35,000 g/mol).

Figure 7A:
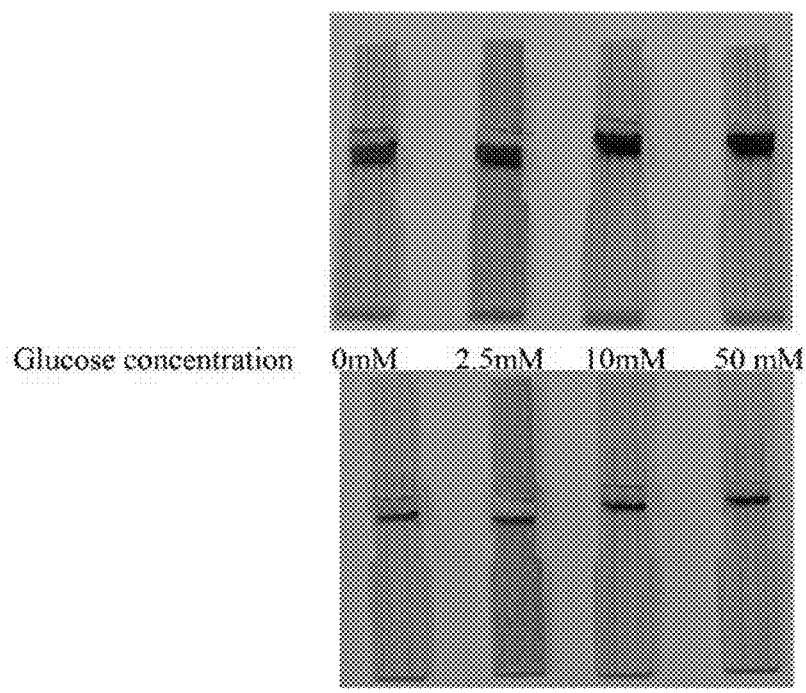
FIGS. 7a and 7b are pictures showing the detection result of the three dimensional lignocellulosic detection device used for detecting glucose.
Figure 7B:
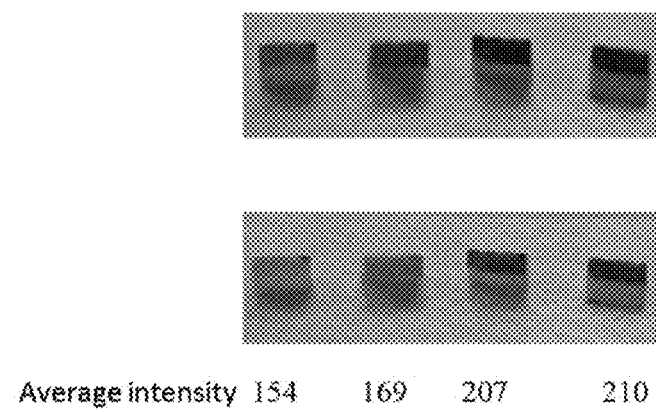

Please refer to FIGS. 7a and 7b which are pictures showing the detection result of the three dimensional lignocellulosic detection device used for detecting glucose. The qualitative result shows that the purple dark coloring result on the detection area of the wood stirrer becomes darker and even with the increasing of glucose concentration. The color difference with the control group may be observed by naked eye on the concentration 2.5 mM. Furthermore, the used wood stirrer may be analyzed independently after detection. The comparison of average color strength with the control group on the concentration 2.5 mM may be easily determined with the assistance with image software (such as Image J).

To sum up, the three dimensional lignocellulosic detection device of the present invention is provided with inherent advantages of the lignocellulosic such as natural material, low cost, easy manipulation and capillary effect and results in a good preventive diagnostic platform. Also, users may achieve preventive disease diagnostics without spending additional time and/or money.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the spirit and scope of the appended claims.

What is claimed is:

1. A three dimensional lignocellulosic detection device, comprising:
   a first lignocellulosic substrate, wherein the first lignocellulosic substrate has a contact area and at least a groove; and
   a second lignocellulosic substrate, arranged in the groove of the first lignocellulosic substrate, wherein materials of the first lignocellulosic substrate and the second lignocellulosic substrate are different, and the second lignocellulosic substrate comprises at least a detection reagent adsorbed to the second lignocellulosic substrate, whereby a liquid specimen contacts the contact area of the first lignocellulosic substrate, the liquid specimen is capable of being absorbed into the first lignocellulosic substrate and flowing to the second lignocellulosic substrate relying on capillarity, and the liquid specimen is capable of reacting with the detection reagent of the second lignocellulosic substrate to achieve the detection of the liquid specimen, wherein the first lignocellulosic substrate is a stirrer, a toothpick or a wooden chopstick.

2. The three dimensional lignocellulosic detection device of claim 1, wherein material of the first lignocellulosic substrate is bamboo.

3. The three dimensional lignocellulosic detection device of claim 1, wherein the surface of the first lignocellulosic substrate is waterproof processed.

4. The three dimensional lignocellulosic detection device of claim 1, wherein shape of the groove is selected from the group consisting of cuboid, cube, cylinder, hemisphere, and V-shaped.

5. The three dimensional lignocellulosic detection device of claim 1, wherein material of the second lignocellulosic substrate is denser than material of the first lignocellulosic substrate.

6. The three dimensional lignocellulosic detection device of claim 1, wherein flow rate of the liquid specimen in the first lignocellulosic substrate is faster than flow rate of the liquid specimen in the second lignocellulosic substrate.

7. The three dimensional lignocellulosic detection device of claim 1, wherein the detection reagent comprises a coloring agent or a fluorescent reagent.

8. The three dimensional lignocellulosic detection device of claim 1, wherein the liquid specimen is saliva, blood or urine of a user.

9. The three dimensional lignocellulosic detection device of claim 1, wherein said device is used for detecting glucose, nitrite or a pH value.

* * * * *